United States Patent [19]

Kolde

[11] Patent Number: 4,918,001
[45] Date of Patent: Apr. 17, 1990

[54] METHOD FOR THE DETERMINATION OF PROTEASE INHIBITORS

[75] Inventor: Hans-Jürgen Kolde, Marburg, Fed. Rep. of Germany

[73] Assignee: Behringwerke Aktiengesellschaft, Marburg, Fed. Rep. of Germany

[21] Appl. No.: 903,458

[22] Filed: Sep. 4, 1986

[30] Foreign Application Priority Data

Sep. 6, 1985 [DE] Fed. Rep. of Germany ....... 3531778

[51] Int. Cl.⁴ ............................ C12Q 1/36; C12Q 1/38
[52] U.S. Cl. ........................................... 435/24; 435/23
[58] Field of Search ..................................... 435/23, 24

[56] References Cited

U.S. PATENT DOCUMENTS 3,912,704 10/1975 Singh ..................................... 435/23
4,493,891 1/1985 Travis .................................... 435/23

OTHER PUBLICATIONS

Bang et al.-Chem. Abst., vol. 89 (1978), p. 124, 985g.
Kratasyuk et al.-Chem. Abst., vol. 103 (1985), p. 209, 902k.
Jochum et al.-Chem. Abst., vol. 101 (1984), p. 16, 657j.
Patent Abstracts of Japan, vol. 7, No. 195 (C-183) [1340], Aug. 25, 1983.
Patent Abstracts of Japan, vol. 8, No. 93 (C-220) [1530], Apr. 27, 1984.
Annual Review of Biochemistry, vol. 49, 1980, pp. 593–626, M. Laskowski et al., "Protein Inhibitors of Proteinases".
Experientia, vol. 39, No. 4, Apr. 1983, pp. 374–375, P. Fric et al., "New Low-Molecular Inhibitors of Pancreatic Elastase with Possible In Vivo Application: Alkylamides of N-acylated Tripeptides".
European Patent Application No. 48,989, filed Sep. 29, 1981.
European Patent Application No. 168,738, filed Jul. 8, 1985.
Clinical Chemistry, vol. 29, No. 2, Feb. 1983, pp. 225–236, J. Fareed et al., "Diagnostic Efficacy of Newer Synthetic-Substrates Methods for Assessing Coagulation Variables: A Critical Overview".

*Primary Examiner*—Sam Rosen
*Attorney, Agent, or Firm*—Finnegan, Henderson, Farabow, Garrett and Dunner

[57] ABSTRACT

A method for the determination of a protease inhibitor using a protease which can be inhibited by this inhibitor, and using a substrate for this protease, is described, in which initially a liquid containing the protease inhibitor and the substrate are mixed, then the protease is added, and the rate of hydrolysis of the substrate is determined.

21 Claims, 8 Drawing Sheets

METHOD FOR THE DETERMINATION OF PROTEASE INHIBITORS

The invention relates to a method for the determination of protease inhibitors by use of the appropriate protease and a substrate for this protease.

Protease inhibitors are proteins of the blood plasma which react with protease and regulate their activity. The most important protease inhibitors in the blood are alpha$_2$-macroglobin, alpha$_1$-antitrypsin, antithrombin III (AT III), alpha$_2$-antiplasmin and C1-esterase inhibitor. As do the proteases, the inhibitors also have a more or less high specificity. Reduction in the activity of protease inhibitors may result in life-threatening situations in patients.

Determination of these inhibitors is indicated for such patients in order to be able to have recourse to therapeutic measures in good time. Furthermore, the determination of protease inhibitors is a highly informative diagnostic measure which is carried out during particular types of therapy and generally for the preoperative screening of patients.

Immunological methods are employed for determination of the concentration of protease inhibitors, using nephelometry or turbidimetry, radial immunodiffusion, enzyme or radioimmunoassays and similar methods. However, in principle all the immunological methods hitherto known also detect inactive molecules of protease inhibitors as well as inactive enzyme/inhibitor complexes. However, numerous cases in which protease inhibitors are present in normal concentration, but exhibit reduced or zero activity, are known.

For this reason, these proteins are increasingly being determined by functional methods which utilize their ability to inhibit enzymes. Normally, the enzyme which can be inhibited by the inhibitor which is to be determined is provided in excess and, after the end of the reaction of the protease with the inhibitor in the sample, the remaining activity of the enzyme is determined, for example using a chromogenic substrate (determination of antithrombin III: Thromb.Res. 5, 621–632, 1974).

A variety of protease inhibitors can be measured relatively straightforwardly in this way. The sensitivity, precision and accuracy of these determination has been considerably improved, in particular by use of synthetic substrates such as peptide paranitroanilides or similar compounds which can be determined by photometry or fluorimetry. This has made routine measurement of proteins of this type possible by kinetic or end point methods.

However, the sequence operations in a typical inhibitor determination according to the current state of the art still has weaknesses which make it difficult to carry out these assays. In particular, incubation times of several minutes may be necessary for maximum inhibition of the enzyme, which is present in excess. These incubation times must be followed strictly, since if the incubation is too short the maximum inhibition is not reached and, on the other hand, if the incubation is too long inhibition by non-specific protease inhibitors may occur. Furthermore, prior dilution of the samples is necessary in some cases. In addition, in order to obtain linear kinetics over a period of at least 3 minutes, relatively large amounts of costly chromogenic substrates are necessary for the determination of the remaining enzyme activity. There is a description in Thromb.Res. 25, 245–253 (1982) of how the interaction of a synthetic substrate and thrombin and its inhibitor with AT III can be measured in the presence of heparin. Various amounts of substrate and heparin were added to a constant amount of purified AT III, and kinetic data describing the action of heparin were determined from the non-linear plot of substrate hydrolysis. A similar method for the determination of heparin is described in Clin.Chem. 28, 1521–1524 (1982); however, the analysis time in this case is quite long.

However, it has been found, surprisingly, that determination of the activity of protease inhibitors in plasma is possible when the substrate and protease concentrations, and in the case of AT III, the heparin concentration, are maintained constant, without the need to take account of interference in the sampl by fibrin formation or varying concentrations of fibrinogen, which reacts with thrombin.

Hence the invention relates to a method of the determination of a protease inhibitor using a protease which can be inhibited by this inhibitor, and using a substrate for this protease, which comprises mixing a liquid containing the protease inhibitor, the substrate and the protease, specifically in such a way that the protease is not added until the protease inhibitor and substrate have been mixed, and determining the rate of hydrolysis of the substrate.

This method for the determination of protease inhibitors avoids a number of the disadvantages, which have been detailed above, of other determination methods. The method according to the invention needs no preincubation and can be applied to a large number of enzyme/inhibitor systems.

It is possible using this method to utilize the competition for reaction with an enzyme by, on the one hand, a chromogenic substrate and, on the other hand, the protease inhibitor which is to be analysed in the plasma or serum sample in order to obtain, by photometry, information about the activity of the inhibitor. Because no preincubation and prior dilutions are necessary in this kinetic method, a considerably greater sample throughout per unit time is achieved than with the established end point methods according to the state of the art. In addition, in most cases it is also possible to use smaller amounts of substrate.

It is possible to use as substrate, in particular, a tripeptide or tetrapeptide of the formula I $$A\text{---}B\text{---}C\text{---}D\text{---}R \qquad \text{I}$$

in which A represents the residue of an amino acid in free or protected form, an N-terminal protective group customary in peptide chemistry, or a hydrogen atom, and B, C and D are each the residue of a free or protected amino acid, and R is a chromogenic, fluorogenic or luminogenic radical which can be determined by photometry, fluorimetry or luminescence measurement, or is the radical of a mercaptan which, after hydrolysis of the D—R bond by a reaction which generates a dyestuff, can be determined by photometry.

In one embodiment of the method, the inhibitor is antithrombin III and the protease is thrombin in a concentration of 0.05 to 1, preferably 0.3 to 0.5 U/ml, and the substrate is a synthetic peptide substrate, and use is made of a buffer containing heparin, the concentration of heparin in the assay mixture being 0.02 to 10 units/ml, preferably 2 units/ml.

In one embodiment, the substrate is the isopropylamide of H-D-Phe-Pro-Arg-ANBA (ANBA=5-amino- 2-nitrobenzoic acid) and is used in a concentration of 0.1 to 1 mmol/l, preferably 0.15 to 0.25 mmol/l. However, it is also possible to use other substrates, for example the para-nitroanilide of Tos-Gly-Pro-Arg.

In another embodiment, the protease is factor Xa in a concentration of 0.02 to 1.0 U/ml. preferably 0.08 to 0.12 U/ml, and the substrate is used in a concentration of 0.1 to 1 mmol/l preferably 0.18 to 0.25 mmol/l.

In the embodiment with factor Xa, the substrate is the 2-methoxy-4-nitroanilide of Z-D-Leu-Gly-Arg or the 4-nitroanilide of benzoyl-Ile-Glu(gamma-piperidyl)-Gly-Arg.

In other preferred embodiments, it is possible to determine the protease C1 esterase, the inhibitor being C1 inactivator, the protease elastase, the inhibitor being $alpha_1$-antitrypsin, the protease chymotrypsin, the inhibitor being $alpha_1$-antichymotrypsin, and the proteinase kallikrein, the inhibitor being plasma kallikrein inhibitors, use being made of a substrate suitable for the particular protease.

It is possible to add a buffer substance such as tris, HEPES or EPPS in a concentration of 0 to 0.5 mol/l, preferably 0.03 to 0.1 mol/l, at a pH of 7 to 9, preferably 7.8 to 8.2, and a neutral salt, preferably sodium chloride, in a concentration of 0 to 0.5 mol/l, preferably 0.08 to 0.15 mol/l.

It is possible and advantageous to determine the rate of substrate cleavage by measurement of the amount cleaved at two points in time, the first being 0 to 20, preferably 12 to 18 sec, and the second being 30 to 300, preferably 80 to 120 sec, after addition of the enzyme.

EXAMPLE 1

Determination of antithrombin III using a chromogenic substrate for thrombin (a) Use was made of thrombin reagent from a Behringwerke assay kit (Behrichrom ®, AT III). The reagent is composed of human alpha-thrombin (0.3 IU/ml), heparin (2.5 USP/ml) in tris buffer pH 8.2. The substrate used was the isopropylamide of H-D-Phe-Pro-Arg-5-amino-2-nitrobenzoic acid.

Mixture:
50 $\mu$l of plasma (undiluted)
100 $\mu$l of substrate (conc. 4 mmol/l)
1000 $\mu$l of thrombin reagent.

Figure 1:
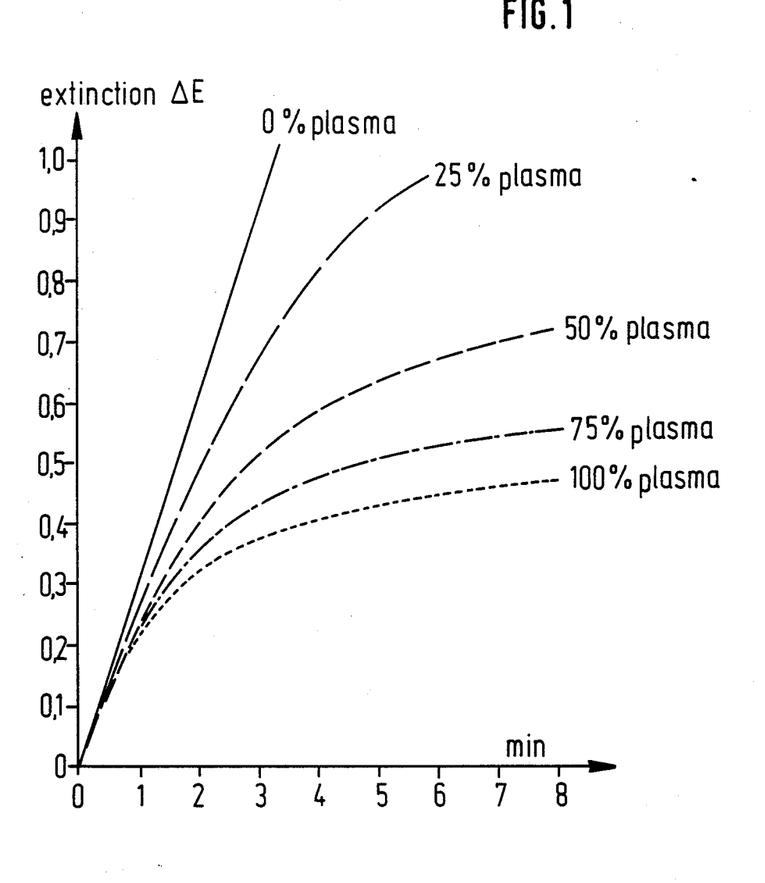

After addition of the thrombin, the absorbance at 405 nm is recorded on a pen recorder. The absorbance/time diagrams for various plasma concentrations and for an enzyme blank with sodium chloride in place of plasma are shown in FIG. 1. It can be seen from this figure that increasing amounts of plasma result in a pronounced deviation of the curve. In contrast, at this substrate concentration the blank is initially completely linear until, owing to substrate depletion, there is a reduction in the reaction rate.

Figure 2:
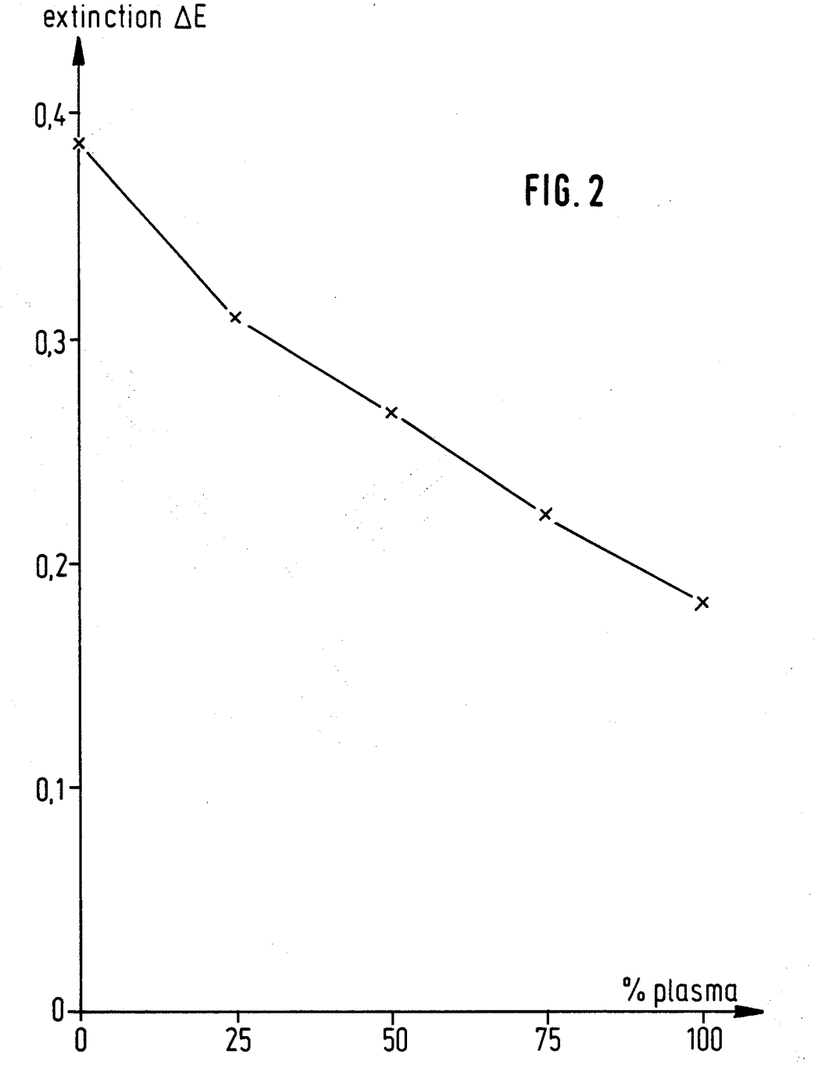

Quantitative information about the content of AT III in the plasma can be derived from these curves. The method which is most straightforward and can be used with many types of apparatus comprises measurement of the absorbance at two different times, for example after 15 and 20 seconds. FIG. 2 shows a calibration plot obtained from the mixture shown above for the absorbance difference between 90 and 15 seconds.

(b) Effect of the substrate concentration on AT III determination

Figure 3:
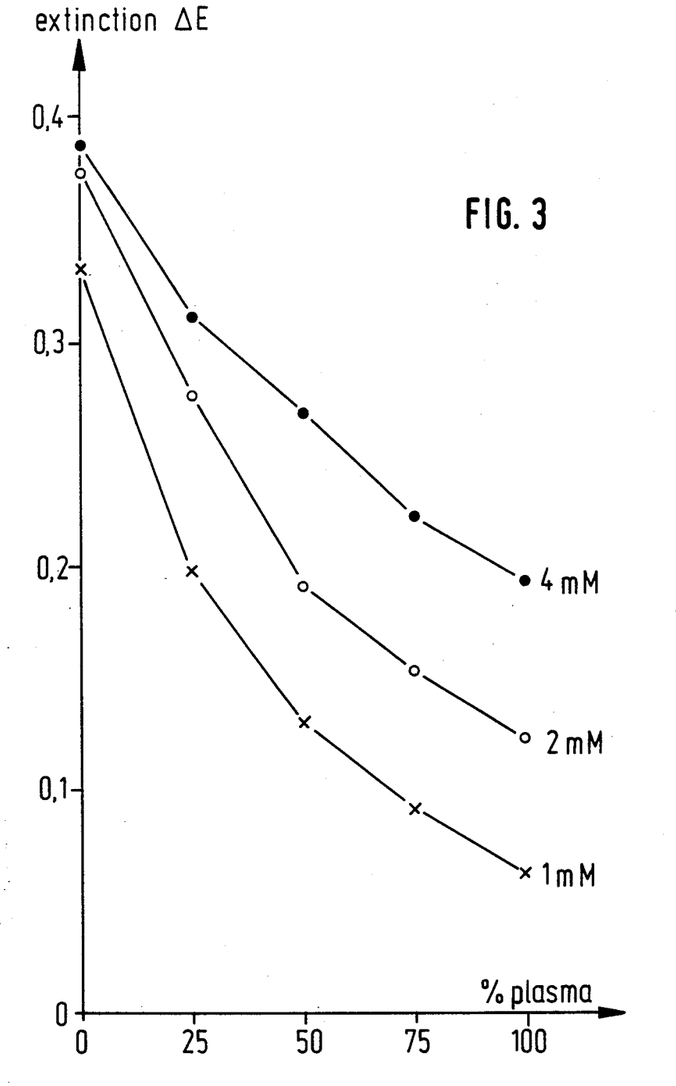

FIG. 3 shows calibration plots obtained with various substrate concentrations. It is clear from this that the highest sensitivity is obtained at low substrate concentration.

(c) Comparison of methods

Figure 4:
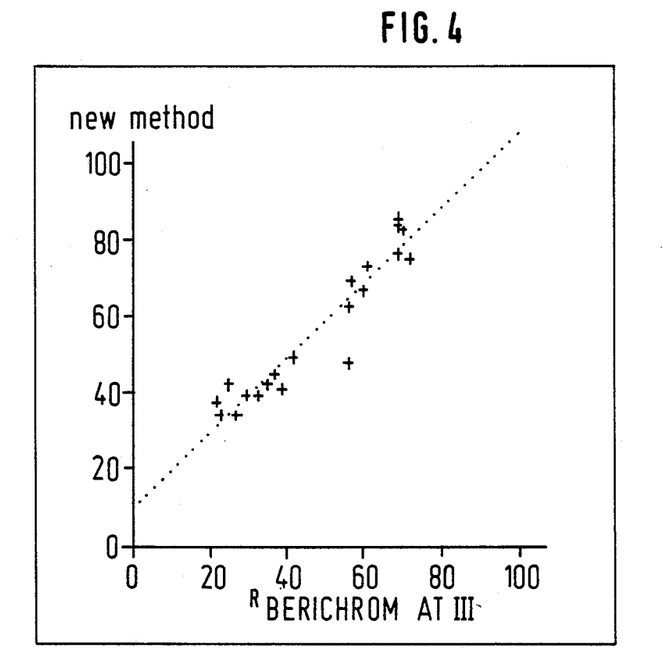

Antithrombin III determination in the simplified form was compared with a determination method according to the state of the art on 20 pathological plasma samples. FIG. 4 shows that the two methods agree very well.

EXAMPLE 2

Determination of antithrombin III via factor Xa

It is also possible to determine antithrombin III via factor Xa. The following mixture was chosen to examine whether the new method is also suitable for this enzyme:
50 $\mu$l of substrate (S-2222, Kabi) 3 mM
50 $\mu$l of plasma
1000 $\mu$l of factor Xa reagent (0.1 U/ml F Xa) in 50 mM TRIS, 100 mM NaCl, 0.2% albumin, 0.2% PEG 6000, 1 U/ml heparin, pH 8.0: (PEG=polyethylene glycol)

Figure 5:
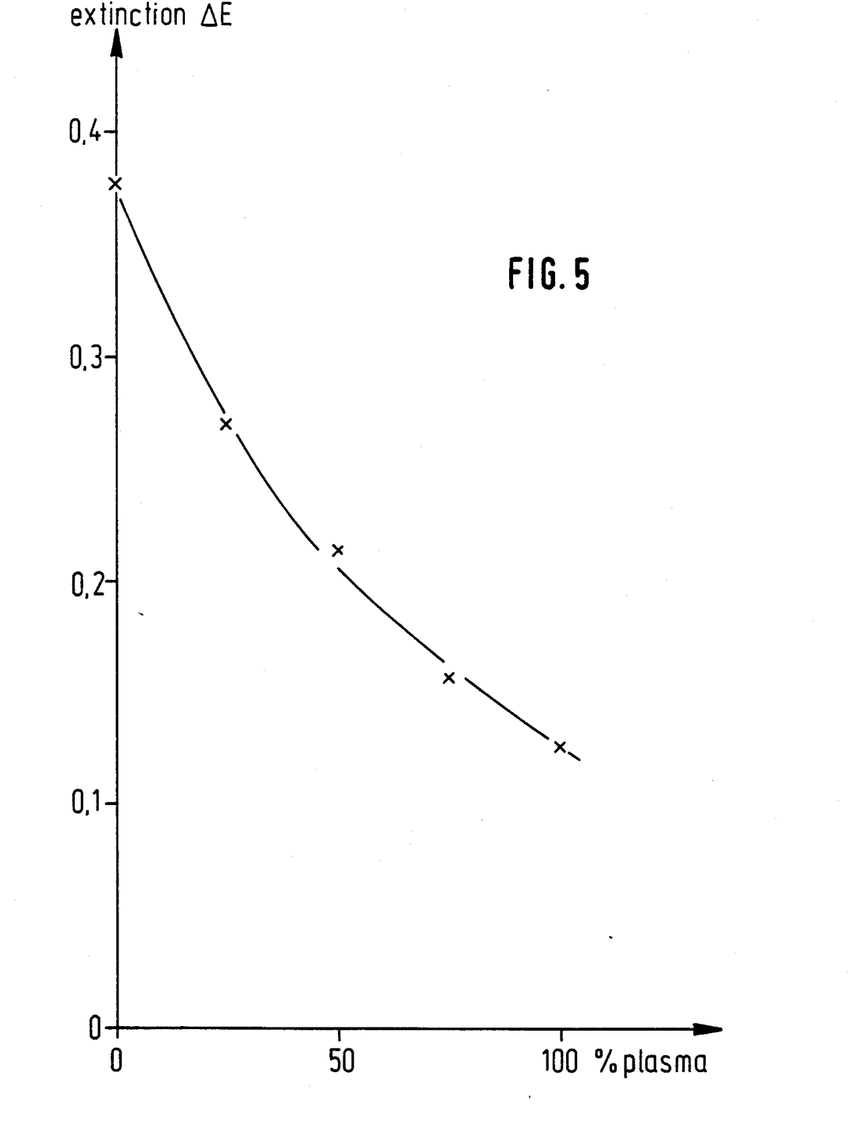

As described in Example 1, an absorbance/time diagram resembling that in FIG. 1 is obtained, from which the reference points shown in FIG. 5 can be constructed by measurement of the absorbance after 15 sec and 105 sec.

EXAMPLE 3

Determination of C1 inactivator

Determination of C1 inactivator via C1 esterase by the new method was carried out as follows:
100 $\mu$l of plasma
50 $\mu$l of chromogenic substrate (para-nitroanilide of N-alpha-methyloxy-carbonyl-epsilon-carbobenzoxy-L-lysyl-glycyl-arginyl), concentration 3 mMol/l
1000 $\mu$l of C1 esterase (2 ATEE/ml in 100 mM sodium phosphate buffer, pH 7.50)

Figure 6:
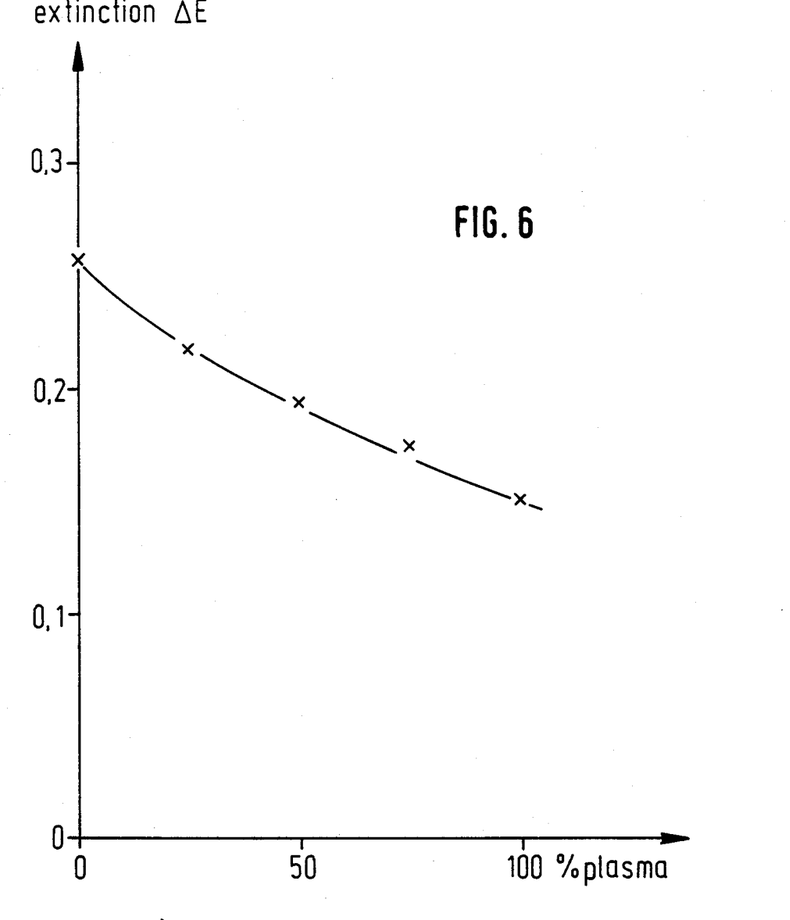

A reference plot derived from a set of curves for various plasma concentrations analogous to that in FIG. 1 is shown in FIG. 6.

EXAMPLE 4

Determination of $alpha_1$-antitrypsin $Alpha_1$-antitrypsin is the most important inhibitor in plasma for elastase, which can be released from, for example, granulocytes. $Alpha_1$-antitrypsin can be determined by inhibition of elastase which is present in excess.

Mixture:
50 $\mu$l of plasma
100 $\mu$l of substrate (2 mMol/l MeO-Suc-(Ala)$_3$-pNA)
50 $\mu$l of esterase (95 U/ml, Sigma)
1000 $\mu$l of buffer, 100 mM tris buffer, 150 mM NaCl, pH 8.2

Figure 7:
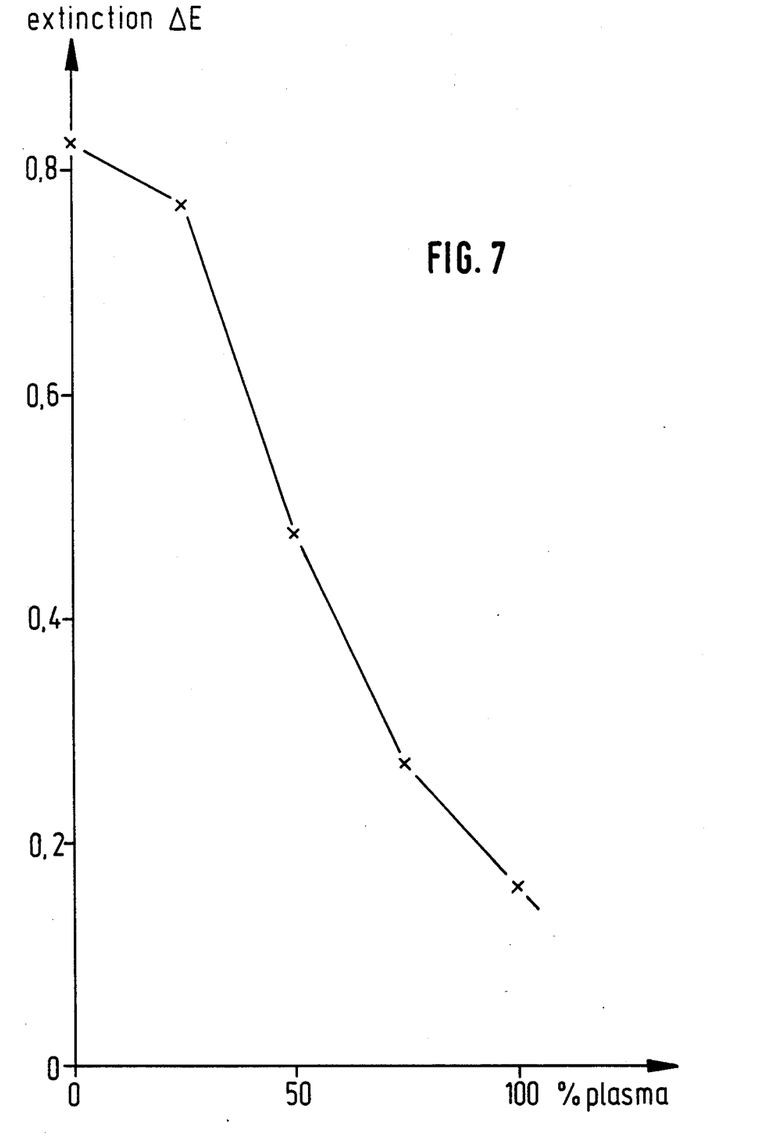

FIG. 7 shows a reference plot for a series of plasma dilutions, which was obtained from evaluation of the set of curves in analogy to Example 1.

EXAMPLE 5

Determination of $alpha_1$-antichymotrypsin $Alpha_1$-antichymotrypsin is a plasma inhibitor which is responsible for inhibition of cellular proteases. It can be determined by inhibition of chymotrypsin.

Mixture:
10 $\mu$l of plasma
500 $\mu$l of substrate (S-2586, Kabi) 2 mM

500 μl of chymotrypsin, 0.001 U/ml in 100 mM tris buffer, 150 mM NaCl pH 8.2)

Figure 8:
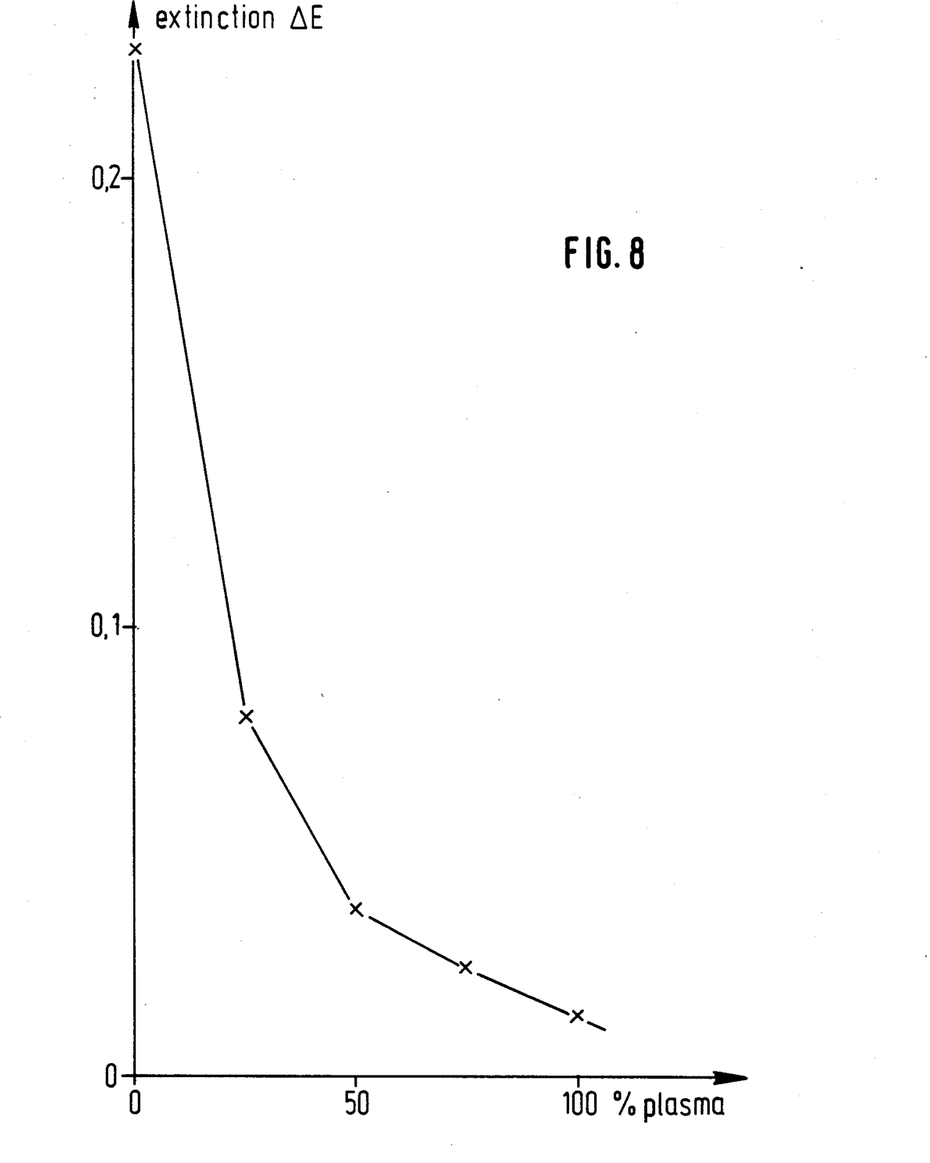

FIG. 8 shows a reference plot obtained for a series of plasma dilutions. The evaluation was carried out in analogy to Example 1.

The examples which have been shown demonstrate the advantage of the method according to the invention. On comparison of the time needed for an AT III determination, for example, the new method proves to be considerably more rapid, with a total duration of about 2 min, than most of the methods of the state of the art, which mostly require about 7 min just for carrying out the analysis, and even more time for the prior dilution of the samples. Although with methods of the state of the art it is also possible to shorten the enzyme/inhibitor reaction, by introducing high doses of the enzyme, in such cases very large amounts of synthetic subtrates are necessary, and the reaction rates become very high and can be measured less well. The disadvantage of sample dilution remains, however, at least with AT III, for which reason the coefficient of variation of the determination is worse than with other methods which do not require an additional dilution step.

I claim:

1. A method for determining the biological activity of a protease inhibitor using a protease which can be inhibited by this inhibitor and a substrate capable of producing a detectable response upon cleavage by the protease, which comprises first mixing a liquid containing the protease inhibitor and the substrate and then adding the protease to start the reaction, and determining the rate of hydrolysis of the substrate.

2. The method as claimed in claim 1, wherein the substrate represents a tripeptide or tetrapeptide of the formula I $$A-B-C-D-R \qquad I$$

in which A is selected from the group consisting of the residue of an amino acid in free or protected form, an N-terminal protective group and a hydrogen atom; B, C and D are each the residue of a free or protected amino acid; and R is selected from the group consisting of a chromogenic, fluorogenic, luminogenic and mercaptan radical.

3. The method as claimed in claim 1, wherein the inhibitor is antithrombin III, the protease is thrombin in a concentration of 0.05 to 1 U/ml, and the substrate is a synthetic peptide substrate, and wherein a buffer containing heparin is added.

4. The method as claimed in claim 1, further comprising adding a buffer substance selected from the group consisting of tris, HEPES and EPPS in a concentration ranging from 0 to 0.5 mol/l at a pH ranging from 7 to 9 and adding a neutral salt in a concentration of 0 to 0.5 mol/l.

5. The method as claimed in claim 1, further comprising adding heparin in a concentration ranging from 0.02 to 10 units/ml.

6. The method as claimed in claim 1, wherein said substrate is the isopropylamide of H-D-Phe-Pro-Arg-ANBA in a concentration ranging from 0.1 to 1 mmol/l.

7. The method as claimed in claim 1, wherein said protease is factor Xa in a concentration ranging from 0.02 to 1.0 U/ml and said substrate is present in a concentration ranging from 0.1 to 1 mmol/l.

8. The method as claimed in claim 7, wherein said substrate is the 2-methoxy-4-nitroanilide of Z-D-Leu-Gly-Arg wherein Z is selected from the group consisting of benzyl, oxyl and carbonyl groups.

9. The method as claimed in claim 1, wherein said protease is C1 esterase and said inhibitor is C1 inactivator.

10. The method as claimed in claim 1, wherein said inhibitor is alpha$_1$-antitrypsin and said protease is elastase.

11. The method as claimed in claim 1, wherein said inhibitor is alpha$_1$-antichymotrypsin and said protease is chymotrypsin.

12. The method as claimed in claim 1, wherein said inhibitor is plasma kallikrein and said protease is kallikrein.

13. The method as claimed in claim 1, wherein the rate of substrate cleavage is determined by measurement of the amount cleaved after 0 to 20 seconds and after 30 to 300 seconds, after addition of the enzyme.

14. The method as claimed in claim 3, wherein said thrombin concentration ranges from 0.15 to 0.5 units/ml.

15. The method as claimed in claim 4, wherein said buffer concentration ranges from 0.03 to 0.1 mol/l at a pH ranging from 7.8 to 8.2.

16. The method as claimed in claim 4, wherein said neutral salt concentration ranges from 0.08 to 0.15 mol/l.

17. The method as claimed in claim 4, wherein said neutral salt is sodium chloride.

18. The method as claimed in claim 5, wherein said heparin concentration is 2 units/ml.

19. The method as claimed in claim 6, wherein said substrate concentration ranges from 0.15 to 0.25 mmol/l.

20. The method as claimed in claim 7, wherein said protease concentration ranges from 0.08 to 0.12 units/ml and said substrate concentration ranges from 0.18 to 0.25 mmol/l.

21. The method as claimed in claim 13, wherein said first measurement is after 12 to 18 seconds and said second measurement is after 80 to 120 seconds.

* * * * *